US008178341B2

(12) United States Patent
Petrucci

(10) Patent No.: US 8,178,341 B2
(45) Date of Patent: May 15, 2012

(54) ELECTROSTATIC PARTICLE EXPOSURE SYSTEM AND METHOD OF EXPOSING A TARGET MATERIAL TO SMALL PARTICLES

(75) Inventor: Giuseppe A. Petrucci, Essex Junction, VT (US)

(73) Assignee: The University of Vermont and State Agricultural College, Burlington, VT (US)

(*) Notice: Subject to any disclaimer, the term of this patent is extended or adjusted under 35 U.S.C. 154(b) by 1034 days.

(21) Appl. No.: 11/844,008

(22) Filed: Aug. 23, 2007

(65) Prior Publication Data

US 2008/0047825 A1 Feb. 28, 2008

Related U.S. Application Data

(60) Provisional application No. 60/840,324, filed on Aug. 25, 2006.

(51) Int. Cl.

| | |
|---|---|
| *C12M 1/42* | (2006.01) |
| *C12M 1/00* | (2006.01) |
| *B01J 19/08* | (2006.01) |
| *H05F 3/00* | (2006.01) |
| *C12N 13/00* | (2006.01) |

(52) U.S. Cl. ............... 435/285.2; 435/285.3; 435/173.1; 435/173.9; 422/186.04; 204/164

(58) Field of Classification Search .................. 204/164; 422/186.04; 435/285.2, 285.3, 173.1, 173.9
See application file for complete search history.

(56) References Cited

U.S. PATENT DOCUMENTS

| | | | | |
|---|---|---|---|---|
| 6,093,557 | A * | 7/2000 | Pui et al. | 435/173.1 |
| 6,929,949 | B1 * | 8/2005 | Hoff et al. | 435/450 |
| 7,892,836 | B2 | 2/2011 | Groisman | |
| 2003/0102444 | A1 * | 6/2003 | Deppert et al. | 250/492.22 |
| 2005/0172735 | A1 * | 8/2005 | Booker | 73/865.5 |

* cited by examiner

*Primary Examiner* — Nathan Bowers
*Assistant Examiner* — Gautam Prakash
(74) *Attorney, Agent, or Firm* — Downs Rachlin Martin PLLC

(57) ABSTRACT

A system for exposing a target material to small particles. The system includes an exposure chamber that receives the target material. A stream of charged particles is directed via an inlet into the exposure chamber toward the target material. One or more electrodes are located relative to the target material and the inlet, and are electrically charged, so as to cause at least some of the charged particles to impact upon the target material. The system can be used to expose the target material to small, for example, nanoscale, particles in a gas environment.

19 Claims, 4 Drawing Sheets

NO VOLTAGE

VOLTAGE

ELECTROSTATIC PARTICLE EXPOSURE SYSTEM AND METHOD OF EXPOSING A TARGET MATERIAL TO SMALL PARTICLES

RELATED APPLICATION DATA

This application claims the benefit of priority of U.S. Provisional Patent Application Ser. No. 60/840,324, filed Aug. 25, 2006, and titled "Electrostatic Particle Exposure System," which is incorporated by reference herein in its entirety.

FIELD OF THE INVENTION

The present invention generally relates to the field of particle delivery. In particular, the present invention is directed to an electrostatic particle exposure system and method of exposing a target material to small particles.

BACKGROUND OF THE INVENTION

At times, it is desirable to deposit small particles, for example, microparticles and nanoparticles, onto a target material or otherwise expose the target material to these small particles. For example, in toxicology some types of toxicity investigations involve exposing cell cultures to particles under investigation. In the size realm of microparticles, the particles under investigation are typically impacted into a cell culture using a gas-jet impaction method. This method involves directing a jet of inert delivery gas containing the particles under investigation toward the cell culture. When the jet is close to the cell culture it is diverted by the culture in accordance with aerodynamic principles. However, because the particles are relatively massive, they cannot change direction as quickly as the gas molecules and continue toward the cell culture until they ultimately impact upon the culture. Of course, the gas-jet impaction method works only so long as the particles under investigation are massive enough so as to not divert around the culture along with the gas molecules.

In the size realm of nanoparticles, the gas-jet exposure method just described is not effective because the particles lack the mass needed for the method to work. When investigating the toxicity of nanoparticles, another type of exposure method is typically used. One such method involves dissolving the particles under investigation in a liquid solvent and exposing the cultured cells to the resulting solution. A shortcoming of this method is that it often does not model reality very well due to the dissolving step and presence of the solvent. This is so in situations wherein the type of cells under investigation, for example, lung cells, when in situ, are exposed directly to the particles and not a liquid solution. In these situations the particle-solution/cultured cell method does not accurately model the in-situ exposure of the actual cells.

SUMMARY OF THE DISCLOSURE

In one embodiment, the present disclosure is directed to a particle exposure system for exposing a target material to charged particles. The particle exposure system includes: an exposure chamber assembly that defines an exposure chamber configured to receive the target material therein, the exposure chamber assembly including: an inlet in fluid communication with the exposure chamber and configured to allow the charged particles to enter the exposure chamber; a material-receiving region configured to receive the target material; at least one outlet located relative to the inlet and relative to the material-receiving region so that when the target material is present in the material-receiving region and a gas is flowed into the exposure chamber via the inlet, the gas flows around the target material; and a first electrode for selectively receiving a first electrical charge and having a predetermined location relative to the material-receiving region and the inlet, the first electrical charge and the predetermined location being selected so that, when the charged particles are present in the exposure chamber and the first electrical charge is applied to the first electrode, the first electrical charge electrically influences charged particles to expose the target material, wherein in the absence of the first electrical charge the charged particles would not have exposed the target material.

In another embodiment, the present disclosure is directed to a particle exposure system for exposing a target material to particles. The particle exposure system includes: an exposure chamber assembly that defines an exposure chamber configured to receive the target material therein, the exposure chamber assembly including: a first electrode; a second electrode spaced from the first electrode; and a material-receiving region located between the first electrode and the second electrode, the material-receiving region configured to receive the target material; and a particle-charging device in fluid communication with the exposure chamber.

In a further embodiment, the present disclosure is directed to a method of exposing a target material to particles. The method includes: providing a target material to be exposed to particles; electrically charging the particles so as to provide electrically charged particles; directing the electrically charged particles toward the target material; and electrostatically influencing the electrically charged particles so as to cause at least some of the electrically charged particles to impact the target material.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
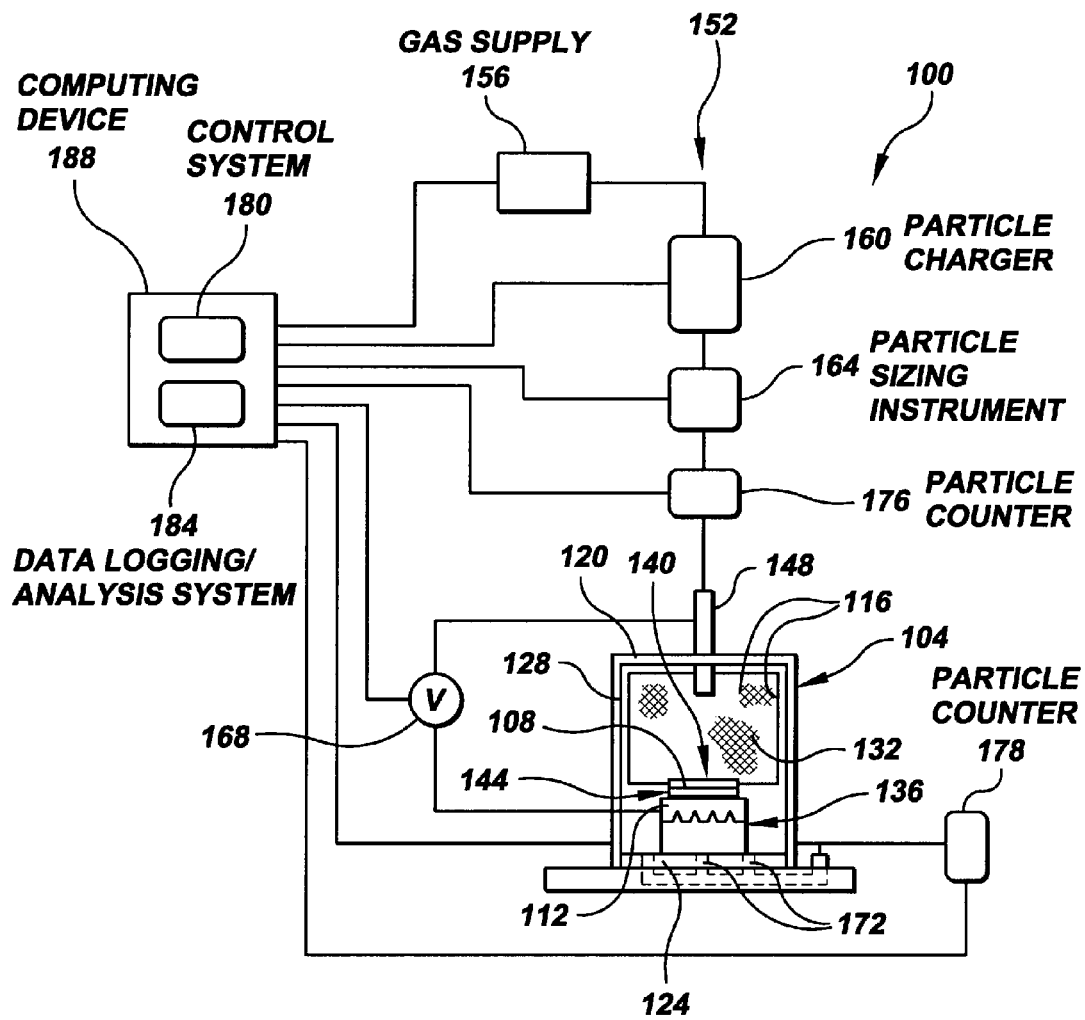
FIG. 1 is a partial high-level block diagram/partial elevational view of an electrostatic particle exposure system made in accordance with the present invention.

Referring now to the drawings, FIG. 1 illustrates an electrostatic particle exposure (EPE) system 100 made in accordance with the present invention. At a high level, EPE system 100 includes an exposure chamber assembly 104 that facilitates controllably exposing a target material 108, such as a cell culture, thin film, advanced material, etc., to small particles (not shown), for example, particles in a range of 10 nm to several μm. In the present context, the term "exposure" and like terms encompass the deposition of at least some of the particles onto target material 108, impacting at least some of the particles into the target material or otherwise allowing at least some of the particles to contact the target material. As discussed below in more detail, the exposing of target material 108 to particles is assisted using electrostatic forces that exist between the particles (which are charged prior to exposing target material 108 thereto) and one or more charged electrodes, such as first and second electrodes 112, 116.

Exposure chamber assembly 104 may include an upper wall 120, lower wall 124 and one or more sidewalls 128 (one in the case of a continuously curved sidewall, such as for a cylindrical wall—more for other shapes) that together define an exposure chamber 132 for containing target material 108 and receiving the particles during use. (It is noted that internal features of exposure chamber assembly 104 are visible in FIG. 1 due to sidewall 128 being translucent in the embodiment shown.) Walls 120, 124, 128 may be made of any suitable material, for example, polycarbonate plastic, among many others. Exposure chamber assembly 104 may also include a pedestal 136 that defines a material-receiving region 140 that receives target material 108. It should be recognized that material-receiving region 140 need not receive only target material 108, but also any appurtenance to the target material that is necessary. For example, when target material 108 is a cell culture, such appurtenances may include a Petri dish 144, cell-growth membrane or other structure for supporting the cultured cells and any growth medium/media needed to sustain the cells.

When pedestal 136 is provided, first electrode 112 may be incorporated into the pedestal or, alternatively may form the entire pedestal. If a pedestal is not provided or a pedestal different from pedestal 136 is provided, first electrode 112 may be located elsewhere, such as adjacent lower wall 124 or incorporated into the lower wall in a suitable manner. First electrode 112 may be made of any suitable electrically conductive material, for example a metal such as copper, among many others. In other embodiments, first electrode 112 may take another form, such as a plate, mesh, coil, etc., or any combination thereof. Second electrode 116 is spaced from first electrode and may also be made of any suitable conductive material, for example a metal such as copper, among many others. In the embodiment shown, second electrode 116 is a cage electrode made of a conductive mesh that extends along upper wall 120 and sidewall 128. In other embodiments, second electrode 116 may take another form, such as a plate, ring, cylinder, coil, etc., or any combination thereof.

The particles may be delivered to exposure chamber 132 via an inlet structure 148 by a particle delivery system 152 that utilizes a carrier gas (not illustrated) for carrying the particles into the chamber and directing the particles toward target material 108. Particle delivery system 152 may include, among other things, a gas supply 156 (a tank, pump, etc.) and a particle charger 160 for imparting the appropriate static electrical charge to the particles provided to exposure chamber 132. Particle delivery system 152 may also include a particle-sizing instrument 164 that selects and provides only particles of one or more desired sizes or one or more size ranges to chamber 132. An example of particle-sizing instrument 164 is Differential Mobility Analyzer Model 3080 available from TSI, Inc., Minneapolis, Minn. Other such instruments are commercially available. It is noted that inlet structure 148 may be electrically conductive, for example, made of copper, and may be electrically connected to second electrode 116 so as to be part of the second electrode. In other embodiments, inlet structure 148 may be nonconductive and/or not part of second electrode 116. First and second electrodes 112, 116 may be electrically connected to a voltage supply 168, for example, a commercially available variable voltage supply, for applying a voltage across the electrodes of a magnitude suitable to subject the particles within chamber 132 to the desired electrostatic forces. Applicable working voltage ranges of, for example, 0 V to 10,000 V are defined by particle size, particle charge, gas flows (i.e., velocity), electrode configuration, electrode spacing, etc.

To control the flow of the particles and gas within exposure chamber 132 during use, exposure chamber assembly 104 may include one or more outlets 172 for exhausting the gas or gas/particle mixture from the chamber. As discussed below in more detail, outlets 172 are preferably located relative to inlet structure 148 and target material 108 so that the stream of gas/particles entering through the inlet structure passes around the target material while maintaining a relatively laminar flow profile. Based on the configuration shown in which target material 108 sits atop pedestal 136 that is concentric with lower wall 124 of chamber 132, outlets 172 are located in lower wall 124 proximate the side wall 128. In this manner, the gas stream, which is directed at the center of target material 108, can readily flow over and to the sides of the target material and pedestal 136. To facilitate the counting of the particles, EPE system 100 may include one or more particle counters 176, 178 in fluid communication with, respectively, inlet structure 148 and outlets 172. Suitable particle counters, for example, condensation particle counters, are commercially available. An example particle counter suitable for use as either particle counter 176, 178 is model 3010 or 3025, available from TSI, Inc., Minneapolis, Minn.

Not shown in FIG. 1 are various other components of EPE system 100, such as valves, conduit, wiring, relays, sensors, etc. as needed to make the system fully functional. Those skilled in the art will readily understand how to utilize these components in the context of the present invention so as to make fully functioning systems and methods without undue experimentation. That said, it is noted that EPE system 100 may include a centralized or decentralized control system 180 operatively connected to the various components of the system, such as particle delivery system 152, flow controls (not shown), for example, valves, voltage supply 168, relays (not shown), particle charger 160, particle sizing instrument 164 and particle counters 176, 178, for controlling the operation of the system. In addition, EPE system 100 may also include a data logging/analysis system 184 for acquiring data regarding the functioning of the system. In some embodiments one, the other, or both of control system 180 and data logging/analysis system 184 may be implemented using a general purpose computing device 188, such as a personal computer, personal digital assistant, etc. In other embodiments one, the other, or both systems 180, 184 may be implemented in an application specific device, such as an application specific integrated circuit, system on chip, or programmable logic device, among others. Those skilled in the art will readily understand how to implement a suitable control system for the various components selected for EPE system 100 and for the degree of automation, centralized control and/or operating convenience desired.

Figure 2A:
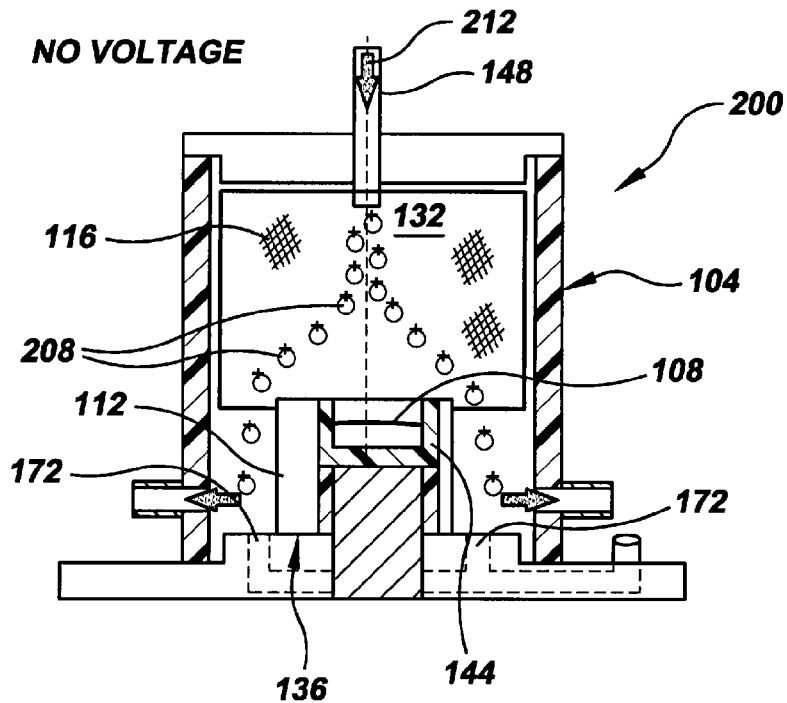
FIG. 2A is an enlarged cross-sectional view of the exposure chamber assembly of FIG. 1 during use with no voltage applied to the electrodes.
Figure 2B:
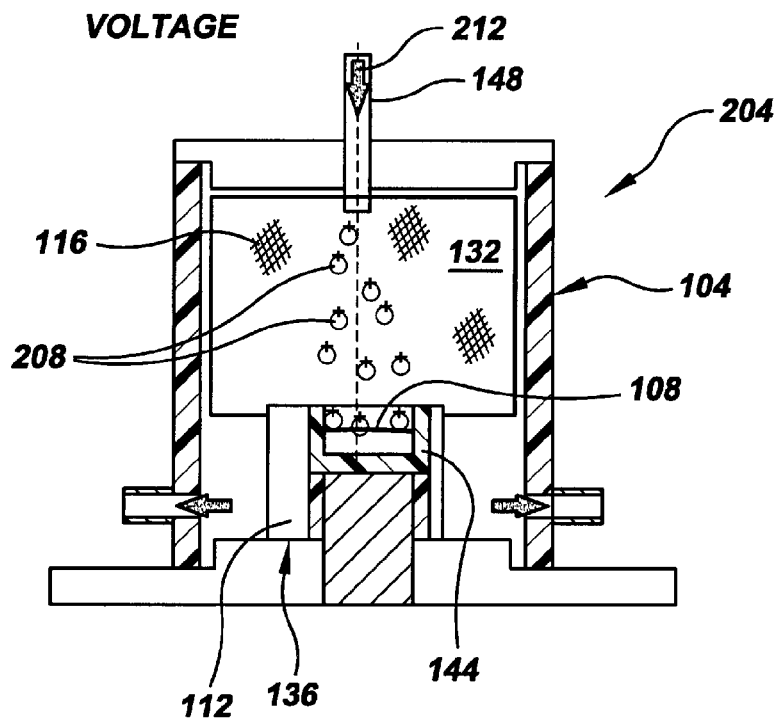
FIG. 2B is an enlarged cross-sectional view of the exposure chamber assembly of FIG. 1 during use with a voltage applied to the electrodes.
Figure 3:
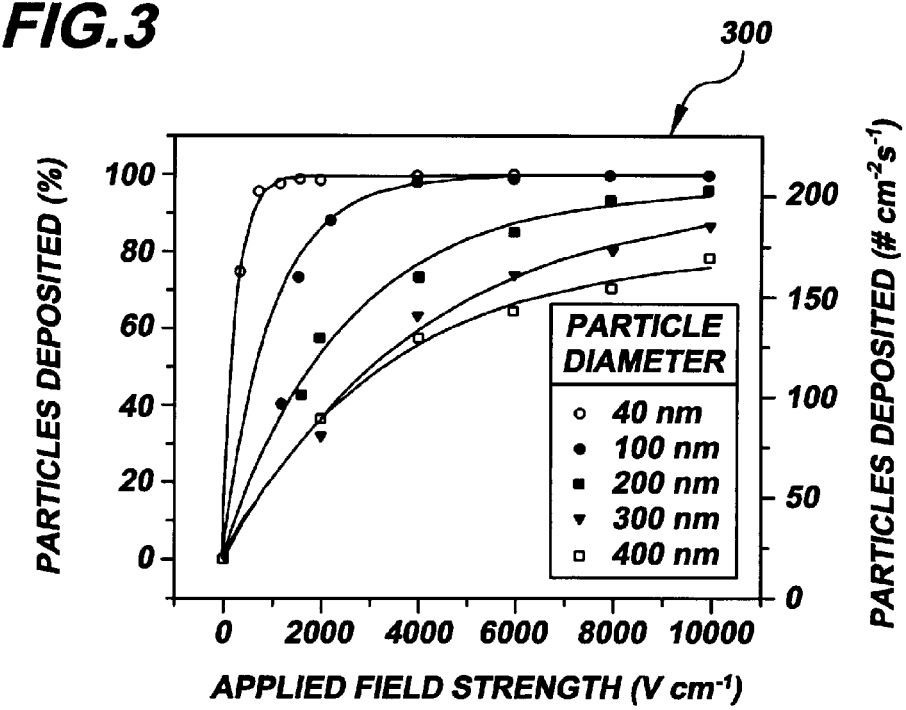
FIG. 3 is a graph illustrating typical particle deposition efficiencies for a particular working example of an exposure chamber assembly made in accordance with the present invention.
Figure 4:
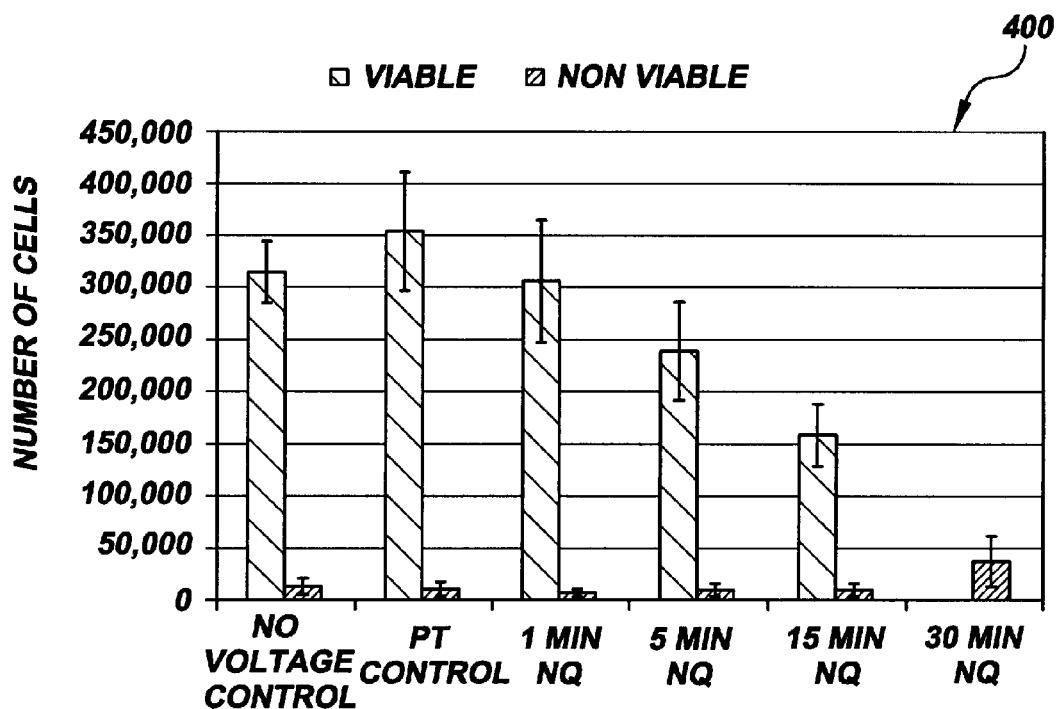
FIG. 4 is a graph illustrating measured dose-mediated cell death for murine epithelial cells after controlled exposure to 1,2-naphthaquinone particles of 150 nm diameter using an exposure chamber assembly made in accordance with the present invention.
Figure 5:
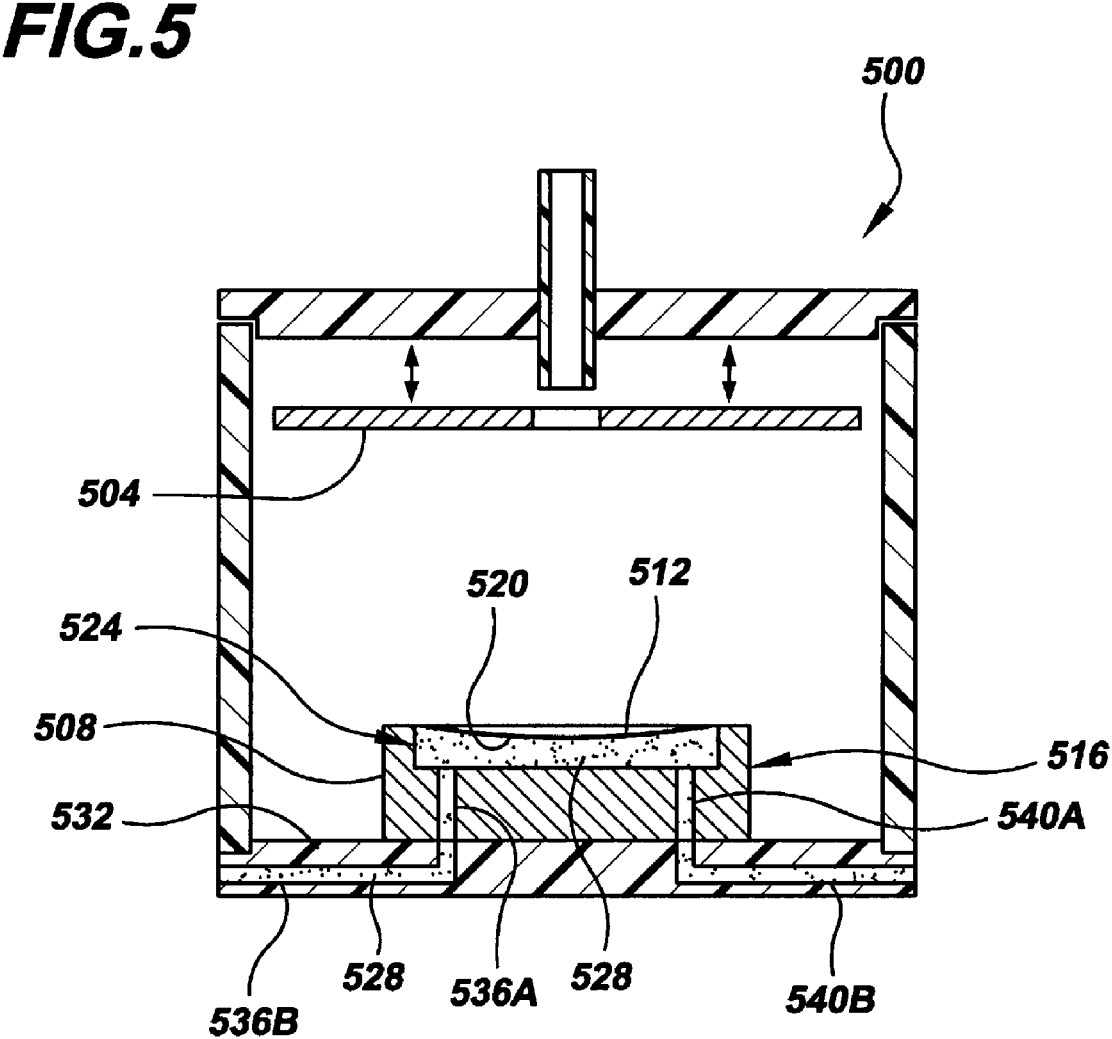
FIG. 5 is a cross-sectional view of an alternative exposure chamber assembly made in accordance with the present invention that may be incorporated into the electrostatic particle exposure system of FIG. 1.

FIGS. 2A-B illustrate two states 200, 204 of exposure chamber assembly 104 of FIG. 1. State 200 of FIG. 2A may be referred to as a "quiescent state." This is a state in which charged particles 208 are being flowed into exposure chamber 132 using a gas stream 212, but there is no voltage applied across first and second electrodes 112, 116. Gas stream 212 and charged particles 208 are directed toward target material 108 by inlet structure 148. As gas stream 212 and charged particles 208 near target material 108, both the gas molecules and charged particles divert around the target material, Petri dish 144 and pedestal 136 due to their low mass as they proceed toward outlets 172. In this state, effectively none of charged particles 208 impact or otherwise contact target material 108.

State 204 of FIG. 2B may be referred to as an "exposure state." As in quiescent state 200, in exposure state 204 charged particles 208 are flowed into exposure chamber 132 using gas stream 212. However, in exposure state 204, a suitable voltage, for example, 10 V to 10,000 V, is applied across first and second electrodes 112, 116 so that electrostatic forces direct the low-mass charged particles 208 in gas stream 212 toward target material 108 rather than being diverted around the target material like the gas molecules. When charged particles 208 have a positive electrical charge as shown, a voltage is applied across first and second electrodes 112, 116 so that the first electrode has a negative electrical charge and the second electrode has a positive electrical charge. In this manner, the positively charged particles 208 are attracted to first electrode 112 and repelled by second electrode 116 so as to divert the charged particles from the flow path that they would take around target material 108 in the absence of any influencing electrical charges. In diverting charged particles 208 toward first electrode 112 and away from second electrode 116, at least some are directed to impact upon target material 108, thereby exposing the target material to the particles. Of course, if charged particles 208 are negatively charged, the polarities of first and second electrodes 112, 116 would be reversed so that the first electrode has a positive charge and the second electrode has a negative charge.

It is noted that although electrodes 112, 116 are shown as being located inside exposure chamber 132, one, the other or both of the positive and negative electrodes may be located outside of the chamber. It is further noted that the illustration of single inlet structure 132 delivering particles in a vertically downward direction (relative to the proper orientation of the attached figures) is merely exemplary. Those skilled in the art will appreciate that the delivery of charged particles 208 may be from more than one inlet structure and/or may be from another direction, such as laterally sideways or vertically upward (again, relative to the figures), even when the exposure surface of the target material, here target material 108, is substantially horizontal. In this connection, it is noted that for embodiments designed for terrestrial use, the exposure surface(s) of the target material may have any suitable orientation relative to Earth's gravity. In such embodiments, the inlet structure(s) provided may deliver the charged particles from any suitable direction(s).

FIG. 3 contains a graph 300 illustrating particle deposition efficiencies for an actual working embodiment of exposure chamber assembly 104 depicted in FIGS. 1 and 2A-B. The charged particles (corresponding to charged particles 208 of FIGS. 2A-B) represented in graph 300 were charged particles of 1,2-naphthaquinone. The data represented in graph 300 was acquired from a plurality of experiments in which the parameters of field strength of the charge applied across first and second electrodes (FIGS. 1 and 2B) and particle size were each varied over respective ranges of 0 V/cm to 10,000 V/cm and 40 nm to 400 nm. As can be readily seen from graph 300 of FIG. 3, 100% of the smallest particles tested were deposited at a field strength of less than 2,000 V/cm. Even with the largest particle size tested, wherein the particles were an order of magnitude larger in diameter than the smallest particle size tested, about 78% of the particles were deposited at 10,000 V/cm. The results achieved were highly repeatable. Different embodiments may be used to efficiently and controllably deposit larger particles (e.g., >400 nm) with 100% efficiency.

FIG. 4 contains a graph 400 illustrating measured cell death for murine lung epithelial cells after controlled exposure to 1,2-naphthaquinone particles (NQ in the graph) having diameters of 150 nm using an actual working embodiment of the exposure chamber assembly 104 depicted in FIGS. 1 and 2A-B. No voltage control shows that application of the high voltage exerts no measurable stress on the cells. PT control indicates the number of viable cells remaining after exposure of the cells for five minutes to 150 nm polystyrene spheres (negative control, i.e., no toxicity to the cells is expected). The graph shows on the y-axis the number of viable (i.e., living) cells remaining after a predefined exposure of the cells to the particles. Shown on the x-axis is the total time of exposure of the cells to the particles. This time may be converted readily to the total number, surface area, volume and/or mass of particles deposited into/onto the target. As seen in graph 400, there is a clear dose-response relationship, which supports use of an exposure chamber assembly, EPE system and method that is in accordance with the present invention.

FIG. 5 illustrates an alternative exposure chamber assembly 500 that may be used in an EPE system made in accordance with the present invention, such as EPE system 100 of FIG. 1. If exposure chamber assembly 500 of FIG. 5 is used with EPE system 100 of FIG. 1, it may be used either in place of exposure chamber assembly 104 or in concert with exposure chamber assembly 104. Those skilled in the art will appreciate the changes that would need to be made in either case.

Exposure chamber assembly 500 of FIG. 5 is identical to exposure chamber assembly 104 of FIG. 1 except for three differences. The first and second differences are that instead of second electrode 504 being a fixed mesh-cage electrode, second electrode 504 is a movable plate electrode that is movable in a direction toward and away from first electrode 508. This movability allows a user to adjust the electrical field strength by adjusting the distance between first and second electrodes 508, 504. While not shown, first electrode 508 may alternatively or additionally be made movable relative to second electrode 504. The third difference is that exposure chamber assembly 500 of FIG. 5 is especially set up for handling cell cultures grown at the air-liquid interface as the target material 512 to be exposed to the charged particles (not shown). In particular, exposure chamber assembly 500 includes a pedestal 516 configured to growing cell cultures on a membrane 520, rather than in a Petri dish. Pedestal 516 includes a growth-medium reservoir 524 for providing a growth medium 528 to membrane. Pedestal 516 and lower wall 532 may include corresponding respective inlets 536A-B and outlets 540A-B for conducting growth medium 528 to and from growth-medium reservoir 524. First electrode 508 may be located immediately adjacent to growth-medium reservoir 524 and may also be in electrical contact with growth medium 528. The electrostatic features of exposure chamber assembly 500 may work as described above relative to exposure chamber assembly 104.

It is noted that while each of exposure chamber assemblies 104, 500 has been described as having only a single exposure chamber, other embodiments may have two or more exposure chambers. Alternatively, as suggested above, an EPE system made in accordance with the present invention may include a plurality of single-chamber exposure chamber assemblies. Likewise, an EPE system made in accordance with the present invention may include a plurality of multi-chamber exposure chamber assemblies (not shown) or one or more multi-chamber exposure chamber assemblies in combination with one or more single-chamber exposure chamber assemblies.

Advantages of an EPE system, such as EPE system 100 of FIGS. 1 and 2A-B, over conventional non-electrostatic impaction particle exposure systems include:

There are no particle-size dependent effects. Non-electrostatic impaction systems are dependent upon particle inertia as the driving force to deposit the particles in the target material, for example, cell culture. As such, smaller particles are deposited with lower efficiency than larger particles. In an EPE system of the present invention, on the other hand, the system may be designed so that it deposits all particles having diameters within a range of about 10 nm to about 1 µm with one hundred percent efficiency. Larger particles are deposited with an accurately known efficiency.

The exposed target material is not disturbed significantly. Conventional systems of which the present inventor is aware rely on impinging a high velocity air jet containing the particles onto a cell culture, thereby causing a disruption of the cells.

Multiple target materials, for example, cell cultures, can be exposed simultaneously.

One or more target materials can be readily exposed to both monodisperse (i.e., particles having the same diameter) or polydisperse (i.e., particles having many particle diameters).

Cells grown at an air/liquid interface can readily be exposed. A non-electrostatic impaction system using a high-velocity air jet would significantly disrupt the thin layer of cells, thereby precluding its use. Typical gas flows that may be used are in the range of less than 10 sccm to greater than 1,000 sccm.

One or more target materials can be exposed to both gases and aerosol particles simultaneously. This is generally not possible with existing non-electrostatic impaction systems because of the high gas velocities needed to impact the aerosol particles.

An advantage of an EPE system of the present disclosure, such as EPE system 100 of FIGS. 1 and 2A-B, over conventional solution exposure systems (see the Background section above) is that, for certain types of situations, it provides a more accurate model of these situations. In one example, a conventional solution exposure system was used with a particular culture of a certain type of cells. A high dose of particles was dissolved in a solution to which the culture was exposed. About 20% of the cells became non-viable in response to the exposure. A similar culture of the same type of cells was then exposed to a much lower dosage of particles (factor of 10,000) using an EPE system made in accordance with the present invention. All of the cells became non-viable in response to the exposure.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A particle exposure system, comprising:
    an exposure chamber assembly that defines an exposure chamber and includes:
        at least one fluid outlet;
        a pedestal having a target-receiving region, said pedestal extending into said exposure chamber so as to space said target-receiving region from said at least one fluid outlet;
    a target containing viable biological material, said target located upon said pedestal in said target-receiving region;
    a particle source containing particles having a diameter from about 10 nm to about 1 µm, said particles selected as a function of said biological material in order to study toxicity of said particles on said biological material, wherein said particle source is fluidly connected to said exposure chamber so as to provide said particles to said exposure chamber;
    a particle charging system operatively configured and located so as to charge said particles with a first electrical charge before said particles enter said exposure chamber from said particle source;
    a gas supply containing a gas, said gas supply designed, configured, and fluidly connected to said exposure chamber so that said gas carries said particles into said exposure chamber;
    a first electrode located at least partially within said pedestal;
    an electrical system operatively connected to said first electrode so as to provide said first electrode with a second electrical charge having a polarity opposite said first electrical charge; and
    a control system designed and configured for controlling the particle exposure system, wherein said control system is set so that said particles from said particle source are deposited onto said target by electrostatic attraction between said particles and said first electrode substantially only when:
        said particle charging system is charging said particles with said first electrical charge;
        said gas is carrying said particles into said exposure chamber; and
        said first electrode is charged with said second electrical charge.

2. The particle exposure system according to claim 1, wherein said biological material comprises lung cells.

3. The particle exposure system of claim 1, further comprising a second electrode spaced from said first electrode, said second electrode for receiving a second electrical charge having the same polarity as said first electrical charge.

4. The particle exposure system of claim 3, wherein said exposure chamber assembly further comprises an upper wall and a sidewall extending between said upper wall and said lower wall, said second electrode located proximate said upper wall.

5. The particle exposure system of claim 4, wherein said second electrode extends down at least a portion of said sidewall.

6. The particle exposure system of claim 3, wherein said second electrode is movable relative to said first electrode.

7. The particle exposure system of claim 3, wherein said first electrode is movable relative to said second electrode.

8. The particle exposure system of claim 1, wherein said exposure chamber assembly further includes an inlet for introducing said particles into said chamber, wherein said inlet is conductive and is in electrical communication with said first electrode.

9. The particle exposure system of claim 8, further comprising a particle-sizing device in fluid communication with said inlet.

10. The particle exposure system of claim 1, wherein said pedestal comprises said first electrode.

11. The particle exposure system of claim 1, wherein said biological-material comprises a cell culture.

12. The particle exposure system of claim 1, wherein said exposure chamber assembly further comprises a growth-medium reservoir located in operative relation to said target-receiving region.

13. The particle exposure system of claim 12, wherein said particle exposure system further comprises a growth medium and said exposure chamber assembly further comprises passageways communicating said growth medium to said target-receiving region and from said growth-medium reservoir.

14. The particle exposure system of claim 1, further comprising at least one particle counter in fluid communication with said exposure chamber.

15. The particle exposure system of claim 1, wherein said particles have a diameter range of about 40 nm to about 400 nm.

16. The particle exposure system of claim 15, wherein said particles have a diameter range of about 40 nm to about 200 nm.

17. The particle exposure system of claim 1, further comprising at least one particle counter in fluid communication with said exposure chamber.

18. The particle exposure system of claim 1, further comprising a particle-sizing device in fluid communication with said exposure chamber.

19. The particle exposure system according to claim 1, wherein said particles are suspected toxins to said biological-material target.

* * * * *